United States Patent
Di Padova et al.

(10) Patent No.: US 7,169,389 B2
(45) Date of Patent: Jan. 30, 2007

(54) HUMAN CD154 BINDING MOLECULES AND TREATMENT METHODS

(75) Inventors: Franco E Di Padova, Birsfelden (CH); Walter Schuler, Grenzach-Wyhlen (DE)

(73) Assignee: Novartis AG, Basel (CH)

(*) Notice: Subject to any disclaimer, the term of this patent is extended or adjusted under 35 U.S.C. 154(b) by 672 days.

(21) Appl. No.: 10/221,529

(22) PCT Filed: Mar. 14, 2001

(86) PCT No.: PCT/EP01/02875

§ 371 (c)(1), (2), (4) Date: Sep. 13, 2002

(87) PCT Pub. No.: WO01/68860

PCT Pub. Date: Sep. 20, 2001

(65) Prior Publication Data

US 2004/0038293 A1 Feb. 26, 2004

(30) Foreign Application Priority Data

Mar. 16, 2000 (GB) .................... 0006398.2

(51) Int. Cl.
- *A61K 39/395* (2006.01)
- *C07K 16/28* (2006.01)
- *C12N 15/13* (2006.01)

(52) U.S. Cl. ............... 424/154.1; 424/130.1; 424/133.1; 424/141.1; 424/143.1; 424/144.1; 424/153.1; 424/173.1; 530/387.1; 530/387.3; 530/388.1; 530/388.2; 530/388.22; 530/388.7; 530/388.73; 530/388.75; 536/23.1; 536/23.5; 536/23.53

(58) Field of Classification Search .............. None
See application file for complete search history.

(56) References Cited

U.S. PATENT DOCUMENTS 6,051,228 A  4/2000  Aruffo et al. ............ 424/144.1

FOREIGN PATENT DOCUMENTS

| WO | 96/23071 | 8/1996 |
| WO | 96/33735 | 10/1996 |
| WO | 96/34096 | 10/1996 |
| WO | 99/12566 | 3/1999 |

OTHER PUBLICATIONS

Schuler et al. Transplantation 77 : 717-726, 2004.*
Rudikoff et al., Proc Natl Acad Sci USA 79: 1979-1983, 1982.*
Colman, Research in Immunology 145: 33-36, 1994.*
Kirk et al., "Treatment with Humanized Monoclonal Antibody Against CD154 Prevents Acute Renal Allograft Rejection in Non-human Primates", Nature Medicine, vol. 5, No. 6, pp. 686-693 (1999).
Chambers-Slater et al., "A Humanized Anti-Human CD154 Monoclonal Antibody Blocks CD154-CD40 Mediated Human B Cell Activation", The FASEB Journal, vol. 13, No. 5, Part 2, p. A988 (1999).

* cited by examiner

*Primary Examiner*—Phillip Gambel
(74) *Attorney, Agent, or Firm*—Thomas R. Savitsky (57) ABSTRACT

A CD154 binding molecule, in particular an antibody to human CD154, especially a human antibody to human CD154 is provided, wherein the CDRs of the heavy chain and light chain have amino acid sequences as defined, for use in the treatment and/or prevention of diseases or disorders wherein CD154 modulation and/or interference with or inhibition of the CD154:CD40 interactions is therapeutically beneficial.

11 Claims, 5 Drawing Sheets

Anti-CD 154 Antibody [µg/ml]    2.0    1.0    0.5    0.25    0.125    None

Fig. 5

SEQUENCE LISTING

```
<160> NUMBER OF SEQ ID NOS: 10

<210> SEQ ID NO 1
<211> LENGTH: 354
<212> TYPE: DNA
<213> ORGANISM: Mus musculus

<400> SEQUENCE: 1
caggtccagc tggtgcagtc tggggctgag gtgcagaagc ctgggtcctc ggtgaaggtc      60
tcctgcaagg cttctggagg caccttcagc aactttgctt tcaactgggt gcgacaggtc     120
cctggacaag ggcttgagtg gatgggaagg atcctcccta gtcttgatat agcaagctac     180
gcacagaagt tccaggacag agtcacgatt accgcggaca aatccacgag cacagcctac     240
atggagttga gcagcctgag atctgaggac acggccatgt attactgtgc gagagaggtg     300
gatggagggg gttttgacta ctgggccag ggaaccctgg tcaccgtctc ctca            354

<210> SEQ ID NO 2
<211> LENGTH: 118
<212> TYPE: PRT
<213> ORGANISM: Mus musculus
```

<400> SEQUENCE: 2

Gln Val Gln Leu Val Gln Ser Gly Ala Glu Val Gln Lys Pro Gly Ser
1               5                   10                  15

Ser Val Lys Val Ser Cys Lys Ala Ser Gly Thr Phe Ser Asn Phe
            20                  25                  30

Ala Phe Asn Trp Val Arg Gln Val Pro Gly Gln Gly Leu Glu Trp Met
        35                  40                  45

Gly Arg Ile Leu Pro Ser Leu Asp Ile Ala Ser Tyr Ala Gln Lys Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Val Asp Gly Gly Gly Phe Asp Tyr Trp Gly Gln Gly Thr
            100                 105                 110

Leu Val Thr Val Ser Ser
            115

<210> SEQ ID NO 3
<211> LENGTH: 321
<212> TYPE: DNA
<213> ORGANISM: Mus musculus

<400> SEQUENCE: 3
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgttcac tttcggcgga     300
gggaccaagg tggagatcaa a                                                321

<210> SEQ ID NO 4
<211> LENGTH: 107
<212> TYPE: PRT
<213> ORGANISM: Mus musculus

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Gly Gly Thr Lys Val Glu Ile Lys
            100                 105

<210> SEQ ID NO 5
<211> LENGTH: 5

```
<212> TYPE: PRT
<213> ORGANISM: Mus musculus

<400> SEQUENCE: 5

Asn Phe Ala Phe Asn
1               5

<210> SEQ ID NO 6
<211> LENGTH: 10
<212> TYPE: PRT
<213> ORGANISM: Mus musculus

<400> SEQUENCE: 6

Arg Ile Leu Pro Ser Leu Asp Ile Ala Ser
1               5                   10

<210> SEQ ID NO 7
<211> LENGTH: 7
<212> TYPE: PRT
<213> ORGANISM: Mus musculus

<400> SEQUENCE: 7

Glu Val Asp Gly Gly Gly Phe
1               5

<210> SEQ ID NO 8
<211> LENGTH: 11
<212> TYPE: PRT
<213> ORGANISM: Mus musculus

<400> SEQUENCE: 8

Arg Ala Ser Gln Gly Ile Ser Ser Trp Leu Ala
1               5                   10

<210> SEQ ID NO 9
<211> LENGTH: 7
<212> TYPE: PRT
<213> ORGANISM: Mus musculus

<400> SEQUENCE: 9

Ala Ala Ser Ser Leu Gln Ser
1               5

<210> SEQ ID NO 10
<211> LENGTH: 9
<212> TYPE: PRT
<213> ORGANISM: Mus musculus

<400> SEQUENCE: 10

Gln Gln Tyr Asn Ser Tyr Pro Phe Thr
1               5
```

HUMAN CD154 BINDING MOLECULES AND TREATMENT METHODS

This application is a section 371 application of PCT/EP01/02875.

BACKGROUND OF THE INVENTION

This invention relates to antibodies to human CD154 (CD154 being also known as gp39 or CD40-L) and to the use of such antibodies to inhibit an immune response mediated by CD154-positive cell interactions with CD40 positive cells, e.g in the treatment and/or prevention of diseases or disorders wherein CD154 interference with, modulation and/or inhibition of the CD154:CD40 interactions is therapeutically beneficial, e.g the prevention of cell, tissue or organ graft rejection, the prevention or treatment of autoimmune or inflammatory diseases, atherosclerosis or Alzheimer disease.

Cell-surface molecules which mediate contact-dependent helper-effector functions of T cells are important for inducing immune responses which require T cell help. For example, the interactions of CD154 on T cells with CD40 on B cells play a central role in activating B cell responses to antigens. It has also been shown that the inhibition of the interaction between CD154 and its receptor CD40 prevents T cell activation and may induce antigen-specific T cell or B cell tolerance. However CD154/CD40 interactions are not restricted to T and B cells or antigen-presenting cells (APCs).

Antibodies to CD154 have been proposed as agents blocking the CD154/CD40 interactions: two humanized anti-human CD154 monoclonal antibodies (MAbs) derived from mouse anti-human CD154 MAbs 5c8 and 24-31 are known. However there still exists a need for an effective method of modulating or blocking the CD154/CD40 interaction, e.g. in order to prevent or treat the disorders and diseases as herein indicated, for example to induce specific tolerance in allotransplantation, e.g. ideally by blocking co-stimulatory signals while at the same time allowing antigen-recognition and T cell receptor signalling.

We have now prepared improved antibodies to CD154 for use in the prevention or treatment of disorders, diseases or conditions as described hereinafter.

DETAILED DESCRIPTION OF THE INVENTION

Accordingly the invention provides a CD154 binding molecule which comprises an antigen binding site comprising at least one immunoglobulin heavy chain variable domain ($V_H$) which comprises in sequence hypervariable regions CDR1, CDR2 and CDR3, said CDR1 having the amino acid sequence Asn-Phe-Ala-Phe-Asn (SEQ. ID No.5), said CDR2 having the amino acid sequence Arg-Ile-Leu-Pro-Ser-Leu-Asp-Ile-Ala-Ser (SEQ. ID. No. 6), and said CDR3 having the amino acid sequence Glu-Val-Asp-Gly-Gly-Gly-Phe (SEQ. ID. No. 7); and direct equivalents thereof.

In a first aspect the invention provides a single domain CD154 binding molecule comprising an isolated immunoglobulin heavy chain which comprises a heavy chain variable domain ($V_H$) as defined above.

In a second aspect the invention also provides a CD154 binding molecule comprising both heavy ($V_H$) and light chain ($V_L$) variable domains in which said CD154 binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence as shown in SED. ID No. 5, said CDR2 having the amino acid sequence as shown in SED. ID No. 6, and said CDR3 having the amino acid sequence as shown in SED. ID No. 7, and b) an immunoglobulin light chain variable domain ($V_L$) which comprises in sequence hypervariable regions CDR1', CDR2' and CDR3', said CDR1' having the amino acid sequence Arg-Ala-Ser-Gln-Gly-Ile-Ser-Ser-Trp-Leu-Ala as shown in SED. ID No. 8, said CDR2' having the amino acid sequence Ala-Ala-Ser-Ser-Leu-Gln-Ser as shown in SED. ID No. 9, and said CDR3' having the amino acid sequence Gln-Gln-Tyr-Asn-Ser-Tyr-Pro-Phe-Tyr as shown in SED. ID No. 10;

and direct equivalents thereof.

Unless otherwise indicated, any polypeptide chain is herein described as having an amino acid sequence starting at the N-terminal extremity and ending at the C-terminal extremity. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

By "CD154 binding molecule" is meant any molecule capable of binding to the CD154 antigen either alone or associated with other molecules. The binding reaction may be shown by standard methods including, for example, a bioassay for determining the inhibition of CD154 binding to its receptor or any kind of binding assays, with reference to a negative control test in which an antibody of unrelated specificity, e.g. an anti-CD25 antibody, is used. Advantageously, the binding of the CD154 binding molecules of the invention to CD154 may be shown in a competitive binding assay.

Examples of antigen binding molecules include antibodies as produced by B-cells or hybridomas and chimeric, CDR-grafted or human antibodies or any fragment thereof, e.g. F(ab')$_2$ and Fab fragments, as well as single chain or single domain antibodies.

A single chain antibody consists of the variable domains of antibody's heavy and light chains covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin or from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the more conserved parts of the variable domains, i.e. the framework regions, are derived from an acceptor antibody, e.g. an antibody of human origin. A CDR-grafted antibody may however retain a few amino acids of the donor sequence in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. Nos. 5,545,806, 5,569,825, 5,625,126, 5,633,425, 5,661,016, 5,770,429, EP 0 438474 B1 and EP0 463151 B1.

Particularly preferred CD154 binding molecules of the invention are human antibodies, especially the ABI793 antibody as hereinafter described in the Examples.

Thus in preferred antibodies the variable domains of both heavy and light chains are of human origin, for instance those of the ABI793 antibody which are shown in SEQ. ID. No. 1 and SEQ. ID. No. 3. The constant region domains preferably also comprise suitable human constant region domains, for instance as described in "Sequences of proteins of immunological interest", Kabat E. A. et al, US department of health and human services, Public health service, National Institute of Health.

Hypervariable regions may be associated with any kind of framework regions, though preferably are of human origin. Suitable framework regions are described in Kabat E. A. et al, ibid. The preferred heavy chain framework is a human heavy chain framework, for instance that of the ABI793 antibody which is shown in SEQ. ID. No. 1. It consists in sequence of FR1, FR2, FR3 and FR4 regions. In a similar manner, SEQ. ID. No. 3 shows the preferred ABI793 light chain framework which consists, in sequence, of FR1', FR2', FR3' and FR4' regions.

Accordingly, the invention also provides a CD154 binding molecule which comprises at least one antigen binding site comprising either a first domain having an amino acid sequence substantially identical to that shown in SEQ. ID. No. 2 starting with amino acid at position 1 and ending with amino acid at position 118 or a first domain as described above and a second domain having an amino acid sequence substantially identical to that shown in SEQ. ID. No. 4, starting with amino acid at position 1 and ending with amino acid at position 107.

Monoclonal antibodies raised against a protein naturally found in all humans are typically developed in a non-human system e.g. in mice. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred CD154 binding molecule of the invention is selected from a human anti CD154 antibody which comprises at least
a) an immunoglobulin heavy chain or fragment thereof which comprises (i) a variable domain comprising in sequence the hypervariable regions CDR1, CDR2 and CDR3 and (ii) the constant part or fragment thereof of a human heavy chain; said CDR1, CDR2 and CDR3 having the amino acid sequence as shown in SED. ID No. 5, 6 and 7, respectively, and
b) an immunoglobulin light chain or fragment thereof which comprises (i) a variable domain comprising in sequence the CDR1', CDR2' and CDR3' hypervariable regions and
(ii) the constant part or fragment thereof of a human light chain, said CDR1', CDR2' and said CDR3' having the amino acid sequence as shown in SED. ID No. 8, 9 and 10, respectively;

and direct equivalents thereof.

Alternatively, a CD154 binding molecule of the invention may be selected from a single chain binding molecule which comprises an antigen binding site comprising
a) a first domain comprising in sequence the hypervariable regions CDR1, CDR2 and CDR3, said hypervariable regions having the amino acid sequences as shown in SEQ. ID. No. 5, 6 and 7, respectively;
b) a second domain comprising the hypervariable regions CDR1', CDR2' and CDR3', said hypervariable regions having the amino acid sequences as shown in SEQ. ID. No. 8, 9 and 10, respectively; and
c) a peptide linker which is bound either to the N-terminal extremity of the first domain and to the C-terminal extremity of the second domain or to the C-terminal extremity of the first domain and to the N-terminal extremity of second domain;

and direct equivalents thereof.

As it is well known, minor changes in an amino acid sequence such as deletion, addition or substitution of one or several amino acids may lead to an allelic form of the original protein which has substantially identical properties.

Thus, by the term "direct equivalents thereof" is meant either any single domain CD154 binding molecule (molecule X)
(i) in which the hypervariable regions CDR1, CDR2 and CDR3 taken as a whole are at least 80% homologous, preferably at least 90% homologous, more preferably at least 95% homologous to the hypervariable regions as shown in SEQ. ID. No. 5, 6 and 7, respectively, and
(ii) which is capable of inhibiting the binding of CD154 to its receptor substantially to the same extent as a reference molecule having framework regions identical to those of molecule X but having hypervariable regions CDR1, CDR2 and CDR3 identical to those shown in SEQ. ID. No. 5, 6 and 7, respectively;

or any CD154 binding molecule having at least two domains per binding site (molecule X')
(i) in which the hypervariable regions CDR1, CDR2, CDR3, CDR1', CDR2' and CDR3' taken as a whole are at least 80% homologous, preferably at least 90% homologous, more preferably at least 95% homologous to the hypervariable regions as shown in SEQ. ID. No. 5, 6, 7, 8, 9 and 10, respectively, and
(ii) which is capable of inhibiting the binding of CD154 to its receptor substantially to the same extent as a reference molecule having framework regions and constant parts identical to molecule X', but having hypervariable regions CDR1, CDR2, CDR3, CDR1', CDR2' and CDR3' identical to those shown in SEQ. ID. No. 5, 6, 7, 8, 9 and 10, respectively.

In the present description amino acid sequences are at least 80% homologous to one another if they have at least 80% identical amino acid residues in a like position when the sequence are aligned optimally, gaps or insertions in the amino acid sequences being counted as non-identical residues.

The inhibition of the binding of CD154 to its receptor may be conveniently tested in various assays including such assays as described hereinafter in the text. By the term "to the same extent" is meant that the reference and the equivalent molecules exhibit, on a statistical basis, essentially identical CD154 binding inhibition curves in one of the assays referred to below.

For example, the assay used may be a cell-free competitive binding assay to test the binding inhibition of CD154 to CD40 in the presence of the CD154 binding molecules of the invention.

Most preferably, the CD154 binding molecule of the invention is a human anti-CD154 antibody which comprises at least one binding site comprising
a) one heavy chain which comprises a variable domain having an amino acid sequence substantially identical to that shown in SEQ. ID. No. 2 starting with the amino acid at position 1 and ending with the amino acid at position 118 and the constant part of a human heavy chain; and
b) one light chain which comprises a variable domain having an amino acid sequence substantially identical to that shown in SEQ. ID. No. 4 starting with the amino acid at position 1 and ending with the amino acid at position 107 and the constant part of a human light chain.

The constant part of a human heavy chain may be of the $\gamma_1$, $\gamma_2$, $\gamma_3$, $\gamma_4$, $\mu$, $\alpha_1$, $\alpha_2$, $\delta$ or $\epsilon$ type, preferably of the $\gamma$ type, more preferably of the $\gamma_1$ or $\gamma_4$ type, whereas the constant part of a human light chain may be of the $\kappa$ or $\lambda$ type (which includes the $\lambda_1$, $\lambda_2$ and $\lambda_3$ subtypes) but is preferably of the $\kappa$ type. The amino acid sequence of all these constant parts are given in Kabat et al ibid.

A CD154 binding molecule of the invention may be produced by recombinant DNA techniques. In view of this, one or more DNA molecules encoding the binding molecule may be constructed, placed under appropriate control sequences and transferred into a suitable host organism for expression.

In a very general manner, there are accordingly provided
(i) DNA molecules encoding a single domain CD154 binding molecule of the invention, a heavy or light chain or fragments thereof of a CD154 binding molecule of the invention, and
(ii) the use of the DNA molecules of the invention for the production of a CD154 binding molecule of the invention by recombinant means.

The present state of the art is such that the skilled worker in the art is able to synthetize the DNA molecules of the invention given the information provided herein i.e. the amino acid sequences of the hypervariable regions and the DNA sequences coding for them. A method for constructing a variable domain gene is for example described in EP-A-239,400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in SEQ. ID. No. 5, 6, 7, 8, 9 or 10, respectively. These cassettes are provided with sticky ends so that they can be ligated at the junctions of the framework Furthermore, it is not necessary to have access to the mRNA from a producing hybridoma cell line in order to obtain a DNA construct coding for the MAbs of the invention. Thus PCT application WO 90/07861 gives full instructions for the production of a MAb by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In view of the foregoing no hybridoma or cell line deposit is necessary to comply with the criteria of sufficiency of description.

In a particular embodiment of the invention, the recombinant means for the production of a CD154 binding molecule includes first and second DNA constructs as described below:

The first DNA construct encodes a heavy chain or fragment thereof and comprises
a) a first part which encodes a variable domain comprising alternatively framework and hypervariable regions, said hypervariable regions being in sequence CDR1, CDR2 and CDR3, the amino acid sequences of which are shown in SEQ. ID. No. 5, 6 and 7, respectively; this first part starting with a codon encoding the first amino acid of the variable domain and ending with a codon encoding the last amino acid of the variable domain, and
b) a second part encoding a heavy chain constant part or fragment thereof which starts with a codon encoding the first amino acid of the constant part of the heavy chain and ends with a codon encoding the last amino acid of the constant part or fragment thereof, followed by a stop codon.

Preferably, this first part encodes a variable domain having an amino acid sequence substantially identical to the amino acid sequence as shown in SEQ. ID. No. 2 starting with the amino acid at position 1 and ending with the amino acid at position 118. More preferably the first part has the nucleotide sequence as shown in SEQ. ID. No. 1 starting with the nucleotide at position 1 and ending with the nucleotide at position 354. Also preferably, the second part encodes the constant part of a human heavy chain, more preferably the constant part of the human $\gamma 1$ chain. This second part may be a DNA fragment of genomic origin (comprising introns) or a cDNA fragment (without introns).

The second DNA construct encodes a light chain or fragment thereof and comprises
a) a first part which encodes a variable domain comprising alternatively framework and hypervariable regions; said hypervariable regions being CDR1', CDR2' and CDR3', the amino acid sequences of which are shown in SEQ. ID. No. 8, 9 and 10, respectively; this first part starting with a codon encoding the first amino acid of the variable domain and ending with a codon encoding the last amino acid of the variable domain, and
b) a second part encoding a light chain constant part or fragment thereof which starts with a codon encoding the first amino acid of the constant part of the light chain and ends with a codon encoding the last amino acid of the constant part or fragment thereof followed by a stop codon.

Preferably, this first part encodes a variable domain having an amino acid sequence substantially identical to the amino acid sequence as shown in SEQ. ID. No. 4 starting with the amino acid at position 1 and ending with the amino acid at position 107. More preferably, the first part has the nucleotide sequence as shown in SEQ. ID. No. 3 starting with the nucleotide at position 1 and ending with the nucleotide at position 321. Also preferably the second part encodes the constant part of a human light chain, more preferably the constant part of the human κ chain.

The invention also includes CD154 binding molecules in which one or more of the residues of CDR1, CDR2, CDR3, CDR1', CDR2' or CDR3' are changed from the residues shown in SEQ ID No. 5, 6, 7, 8, 9 or 10, respectively; for instance by mutation e.g. site directed mutagenesis of the corresponding DNA sequences. The invention includes the DNA sequences coding for such changed CD154 binding molecules. In particular the invention includes CD154 binding molecules in which one or more residues of CDR1', CDR2' or CDR3' have been changed from the residues shown in SEQ. ID. No. 8, 9 or 10, respectively.

In the first and second DNA constructs, the first and second parts are preferably separated by an intron. In the intron located between the first and second part, an enhancer may be inserted. The presence of this genetic element which is transcribed but not translated, may be required for an efficient transcription of the second part. More preferably the first and second DNA constructs comprise the enhancer of a heavy chain gene advantageously of human origin.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, a viral promoter may be used, e.g. a cytomegalovirus (CMV), Rous Sarcoma (RSV) or Murine Leukemia (MLV) promoter.

The desired antibody may be produced in a cell culture or in a transgenic animal. A suitable transgenic animal may be obtained according to standard methods which e.g. include micro injecting into eggs the first and second DNA constructs placed under suitable control sequences transferring the so prepared eggs into appropriate pseudo-pregnant females and selecting a descendant expressing the desired antibody.

When the antibody chains have to be produced in a cell culture, the DNA constructs must first be inserted into either a single expression vector or into two separate but compatible expression vectors, the former possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted in two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g. a myeloma, hybridoma or a normal immortalised B-cell, which conveniently does not express any endogenous antibody heavy or light chain.

It is also preferred that the host organism contains a large number of copies of the CD154 binding molecule coding sequence per cell. If the host organism is a mammalian cell line, this desirable goal may be achieved by amplifying the number of copies of the coding sequences according to standard methods. Such amplification methods often consist of selecting for increased resistance to a drug, said resistance being encoded by the expression vector. Preferred systems for expression of the CD154 binding molecules of the invention include Glutamine Synthetase-based systems (GS-based), such as those described in EP 0256055 B, EP 0323997 B and European patent application 89303964.4.

In a further aspect of the invention there is provided a process for the production of a CD154 binding molecule which comprises (i) culturing an organism which is transformed with an expression vector as defined above and (ii) recovering the CD154 binding molecule from the culture.

In a preferred embodiment, transgenic mice engineered to express the human IgG/κ repertoire instead of the murine immunoglobulin repertoire (Fishwild et al., 1996, Nat Biotechnol., 14, 845–851) are used to generate antibodies to human CD154. Mice are repeatedly immunized with a soluble human CD154 recombinant protein consisting of the extracellular domain of human CD154 fused to the mouse Cκ chain (CD154-κ). To make the protein more immunogenic, the soluble CD154 is crosslinked with KLH. Priming with CD154:KLH is followed by repeated immunizations with cells of a recombinant human cell line which constitutively expresses surface CD154. Spleen cells from these mice are immortalized by standard hybridoma technology and murine hybridoma cells are obtained which secrete human anti-CD154 antibodies of the IgG1/κ type. These antibodies are finally selected by their reactivity to human CD154 and by their ability to inhibit the binding of CD154 to CD40 as measured in a competitive ELISA type assay.

In accordance with the present invention it has been found that the CD154 binding molecule as herein disclosed, e.g. a human anti-human, e.g. the ABI793 antibody has a desirable antigen epitope specificity. Thus it has been found that ABI793 recognizes an epitope on both the human as well as the cynomolgus monkey CD154 antigen; this epitope is different from the respective epitope(s) which are recognized by the mouse anti-human CD154 Mabs 5c8 and 24-31. Particularly, while the mouse anti-human Mab 5c8 only recognizes an epitope formed on the trimeric human CD154, the human anti-human ABI793 antibody binds to an epitope present on both the monomeric and trimeric human CD154.

Antibodies, in particular chimeric and CDR-grafted antibodies and especially human antibodies, preferably monoclonal antibodies which have binding specificity for an antigenic epitope of human CD154 different from the respective epitope(s) which are recognized by the mouse anti-human CD154 Mabs 5c8 and 24-31, the antibodies being capable of interfering with, modulating or inhibiting the physiological CD154/CD40 interactions, and use of such antibodies e.g. in the prevention of organ graft rejection or in the prevention or treatment of autoimmune or inflammatory disorders or diseases, atherosclerosis or Alzheimer disease, are novel and are included within the scope of the present invention.

Accordingly the invention also provides a CD154 binding molecule, preferably a human antibody, which specifically binds and forms a complex with a human epitope present on the monomeric as well as the trimeric human CD154, said epitope being the epitope to which ABI793 specifically binds.

CD154 binding molecules in accordance with the present invention, e.g. antibodies, (hereinafter referred to as Antibody of the Invention) exhibit valuable pharmacological properties, e.g. they interfere with, modulate or inhibit the physiological CD154/CD40 interactions, e.g. as demonstrated in standard in vitro and in vivo test methods, for example as described below:

1. Inhibition of CD154:CD40 Binding

The ability to inhibit the binding of CD154 to CD40 is tested in a cell-free competitive binding assay. Recombinant soluble human CD154 (i.e., the extracellular portion of human CD154 fused to mouse $C_\kappa$) is immobilized on microtiter plates and the plates incubated, in the presence or absence of a putative inhibitor, with biotinylated recombinant soluble human CD40. The fraction of CD40 bound to CD154 is fluorimetrically determined using Eu-labelled streptavidin as the detection reagent. In this assay, the Antibody of the Invention has an inhibitory capacity expressed as $IC_{50}$, i.e. the concentration needed to achieve 50% inhibition of the binding, within 5 to 150 ng/ml. ABI793 has been found to have an $IC_{50}$ of 75±11 ng/ml.

The inhibition of the CD154:CD40 binding by the Antibody of the Invention, e.g. ABI793, is specific since it does not inhibit TNF:TNF-RI binding when tested at concentrations which are up to more than 50-fold higher than the $IC_{50}$ found for the CD154:CD40 binding (CD154 and CD40 are members of the TNF and TNF receptor (TNF-R) family, i.e. they share homology with TNF and TNF-R, respectively). The inhibition of the TNF:TNF-RI binding is performed by means of a competitive binding assay set up in the same format as the CD154:CD40 binding assay.

2. Inhibition of CD154/IL-4 driven B Cell Proliferation

Soluble recombinant mouse or human CD154 protein, in combination with IL-4, stimulates purified human B cells which constitutively express surface CD40, to proliferate and to produce immunoglobulin. Briefly, cultures are set up in 96-well flat-bottomed tissue culture clusters (Costar) in RPMI (Gibco) supplemented with Na-pyruvate (1 mM; Gibco), MEM non-essential amino acids (Gibco), 2-mercaptoethanol (50 µM), L-glutamine (2 mM), gentamycin (50 µg/ml; Gibco), bacto asparagine (20 µg/ml; Difco), human insulin (5 µg/ml; Sigma), human transferrin (40 µg/ml; Sigma), and selected fetal calf serum (10%, Hyclone Labs, UT). In standard assays, purified B cells (2.5× $10^5$/ml; 0.2 ml cultures) are stimulated for 5 days in triplicates by recombinant human CD154 (3 µg/ml) and IL-4 (100 U/ml). To assess B cell proliferation, cells are pulsed on day 4 with 1 mCi/well of $^3$H-TdR, and the uptake of radioactivity is determined 16 h later. SD between triplicate cultures are <20%. Control cultures are stimulated with murine CD154. In this assay, the Antibody of the Invention inhibits the CD154-dependent B cell proliferation: ABI793 has been found to have an $IC_{50}$ of 73±21 ng/ml.

3. Induction of B Cell Proliferation by *Staphylococcus aureus* Cowan I Strain (SAC)

SAC activates approximately 20% of human peripheral B cells by crosslinking surface immunoglobulin. Purified B cells (2.5×$10^5$/ml; 0.2 ml cultures) are stimulated in triplicates for 10 days by soluble SAC (Sigma; dilution 1:10,000) and IL-2 (Chiron; 300 U/ml). To assess B cell proliferation, cells are pulsed on day 4 with 1 mCi/well of $^3$H-TdR, and the uptake of radioactivity is determined 16 h later. SD between triplicate cultures are <20%. B cell proliferation triggered with SAC in combination with IL-2, i.e. CD154 independent B cell proliferation, is not inhibited by the Antibody of the Invention, e.g. ABI793, at a concentration about 40-fold higher than the $IC_{50}$.

4. Renal Allografts

Transplantation is done between genetically distinct donor-recipient pairs of cynomolgus monkeys as determined by Mixed Lymphocyte Reaction (MLR). The allograft is implanted using standard microvascular techniques to create an end-to-side anastamosis between the donor renal artery and recipient distal aorta as well as between the donor renal vein and recipient vena cava. A primary ureteroneocystostomy is then created. Bilateral native nephrectomy is completed before closure. The Antibody, e.g. ABI793, is administered intravenously, at a dose of 20 mg/kg at the time of transplantation (Day 0) and then on postoperative days 1, 4, 11, 18 and 28 followed by a single dose every 28 days for 6 months. The thus treated monkeys have been found to show the desired effects.

The Antibody of the Invention is therefore useful in the treatment and/or prevention of diseases or disorders wherein CD154 modulation and/or interference with or inhibition of the CD154:CD40 interactions is therapeutically beneficial, prevention of macrophage-associated inflammatory processes or in the treatment of diseases wherein suppression of antibody responses to antigens are desirable, e.g. inhibition of B cell proliferation and differentiation, inhibition of T cell responses, induction or modulation of T or B cell tolerance or inhibition of the growth of tumor cells expressing CD154 antigen. Such conditions include autoimmune and non-autoimmune disorders. Specific conditions which are potentially treatable by administration of the Antibody of the Invention include e.g. Allergic bronchopulmonary aspergillosis; Autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angioedema, hereditary or idiopathic; Ankylosing spondylitis; Arteritis, cranial, giant cell or temporal; Arteritis, Takayasu's; Asthma; Ataxia-telangiectasia; Autoimmune oophoritis; Autoimmune orchitis; Autoimmune polyendocrine failure; Behcet's disease; Berger's disease; Buerger's disease; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum, multiforme or nodosum; Familial Mediterranean fever; Felty's syndrome; Fibrosis pulmonary, Glomerulonephritis, anaphylactoid, autoimmune, post-streptococcal, or post-transplantation; Glomerulopathy, membranous; Goodpasture's syndrome; Graft-vs.-host disease; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus, foliaceus or vulgaris; Pigeon breeder's disease; Pneumonitis, hypersensitivity; Polyarteritis nodosa; Polymyalgia rheumatica; Polymyositis; Polyneuritis, idiopathic; Portuguese familial polyneuropathics; Pre-eclampsia/eclampsia; Primary biliary cirrhosis; Progressive systemic sclerosis (Scieroderma); Psoriasis; Psoriatic arthritis; Pulmonary alveolar proteinosis or fibrosis, Raynaud's phenomenon/syndrome; Reidel's thyroiditis; Reiter's syndrome, Relapsing polychrondritis; Rheumatic fever, Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Syphilis; Systemic lupus erythematosus; Transplant rejection; Tuberculosis; Ulcerative colitis; Undifferentiated connective tissue disease; Urticaria, chronic or cold; Uveitis; Vitiligo; Weber-Christian disease; Wegener's granulomatosis; Wiskott-Aldrich syndrome; as well as Atherosclerosis, Alzheimer disease, HIV infections, or Lymphoproliferative disorders, e.g. leukemias (e.g. T-cell leukemia) or lymphomas (e.g. T-cell lymphoma). By transplant rejection is meant rejection of an allo- or xenograft, e.g cells, tissues or solid organs, for example pancreatic islets, bone marrow, corneal tissue, neuronal tissue, heart, lung, combined heart-lung, kidney, liver, bowel, pancreas, trachea, oesophagus.

In prevention or prophylactic applications, the CD154 binding molecule of the Invention may be administered to a patient not already in the disease state to enhance the patient's resistance (modulate or suppress an immune response). Such an amount is defined to be a "prophylactically effective dose". A preferred prophylactic use is for the prevention of transplant rejection.

For the above uses the required dosage will of course vary depending on the mode of administration, the particular condition to be treated, the general state of the patient's own immune system, and the effect desired. In general, satisfactory results are indicated to be obtained at dosages of from about 0.05 to 100 mg/kg body weight. The Antibodies of the Invention may be administered by any conventional route, in particular enterally, e.g. orally, e.g. in the form of capsules, or parenterally, e.g. in the form of an injectable solution or suspension, topically or by inhalation (intranasal or oral inhalation).

Pharmaceutical compositions comprising an Antibody of the Invention in association with at least one pharmaceutically acceptable carrier or diluent may be manufactured in conventional manner by mixing with a pharmaceutically acceptable carrier or diluent.

In accordance with the foregoing the present invention further provides:

1. A method for preventing or treating disorders, diseases or conditions such as indicated above, e.g. inhibition of an immune response mediated by CD154-positive cell interactions with CD40-positive cells, inhibition of B cell proliferation and differentiation or T cell responses, induction or modulation of T or B cell tolerance or prevention of macrophage-associated inflammatory processes, in a subject in need of such treatment, which method comprises administering to said subject an effective, non-toxic amount of a CD154 binding molecule as disclosed herein, e.g. ABI793;
2. Use of a CD154 binding molecule as disclosed herein, e.g ABI793, in a method such as indicated above;
3. A pharmaceutical composition, e.g. for use in a method such as indicated above, comprising a CD154 binding molecule as disclosed herein, e.g. ABI 793, in association with a pharmaceutically acceptable diluent or carrier therefor;
4. A CD154 binding molecule as disclosed herein, e.g. ABI793, for use in the preparation of a pharmaceutical composition useful in a method as indicated above.

The CD154 binding molecule, e.g. the Antibody of the Invention, may be administered as the sole active ingredient or in conjunction with, e.g. as an adjuvant to, other drugs in immunosuppressive or immunomodulating regimens or other anti-inflammatory agents, e.g. for the treatment or prevention of allo- or xenograft acute or chronic rejection or inflammatory or autoimmune disorders, or a chemotherapeutic agent. For example, Antibody of the Invention may be used in combination with a calcineurin inhibitor, e.g. cyclosporin A or FK 506; a macrocyclic lactone having immunosuppressive properties, e.g. rapamycin or 40-O-(2-hydroxyethyl)-rapamycin (RAD); an ascomycin having immunosuppressive properties, e.g. ABT-281, ASM981, etc.; corticosteroids; cyclophosphamide; azathioprene; methotrexate; a lymphocyte homing agent, e.g. FTY720; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to CD40 or to other leukocyte receptors, e.g., MHC, CD2, CD3, CD4, CD7, CD8, CD25, CD28, CD80, CD86, CD45 or CD58 or their ligands, or an anti-BB1 monoclonal antibody; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or –3 antagonists, VCAM-4 antagonists or VLA-4 antagonists; or a chemotherapeutic agent, e.g. paclitaxel, gemcitabine, cisplatinum, doxorubicin or 5-fluorouracil.

Where the Antibody of the Invention is administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a CD154 binding molecule as disclosed herein, e.g ABI793, and at least a second drug substance, e.g. an immunosuppressant, immunomodulatory, anti-inflammatory or chemotherapeutic drug, e.g. as indicated above.
6. A pharmaceutical combination, e.g. a kit, for use in any method as defined above, comprising a) a first agent which is a CD154 binding molecule as disclosed herein, e.g ABI793, in free form or in pharmaceutically acceptable salt form, and b) at least one co-agent, e.g. an immunosuppressant, immunomodulatory, anti-inflammatory or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. ABI793 and a co-agent, are both administered to a patient simultaneously in the form of a single entity or dosage. The term "non-fixed combination" means that the active ingredients, e.g. ABI793 and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Preferred combinations are e.g. a combination comprising
a) an Antibody of the Invention, e.g. ABI793, and
b) as a co-agent, CTLA4Ig or a mutant thereof, e.g. LEA29Y;
and/or rapamycin or 40-O-(2-hydroxyethyl)-rapamycin;
and/or a lymphocyte homing agent, e.g. FTY720;
and/or a monoclonal antibody to CD25, e.g. basiliximab or daclizumab.

Examples of preferred combinations are a combination of an Antibody of the Invention with LEA29Y, RAD and optionally FTY720, or a combination of an Antibody of the Invention with LEA29Y and basiliximab or daclizumab, or a combination of an Antibody of the Invention with RAD or a combination of an Antibody of the Invention with LEA29Y. A combination of an Antibody of the Invention with LEA29Y, RAD and optionally FTY720 may be advantageously used to induce or modulate B or T cell tolerance.

Preferably the Antibody of the Invention is a human antibody, most preferably the ABI793 antibody or a direct equivalent thereof.

The invention is further described by way of illustration only in the following Examples which refer to the accompanying Figures.

EXAMPLE 1

Generation of the Hybridoma and Purification of the Antibody

Genetically engineered mouse 66 (Medarex Inc. Annadale, N.J.) is immunized with a soluble human CD154 recombinant protein as described above (50 μg) s.c. in several sites in adjuvant. The mouse is boosted five additional times with the last injection three days before the fusion. On the day of the fusion mouse 66 is killed by $CO_2$ inhalation and spleen cells ($4.1 \times 10^7$) are fused by a routine method using PEG 4000 with an equal number of PAI-O cells, a mouse myeloma cell line. Fused cells are plated out in 624 wells (1 ml/well) containing a feeder layer of mouse peritoneal cells (Balb C mice), in HAT supplemented RPMI 1640, 10% heat inactivated fetal calf serum $5 \times 10^{-5}$ M β-mercaptoethanol. Supernatants are collected and tested in ELISA and screened for CD154 reactive monoclonal antibodies. Five monoclonal antibodies of the IgG/κ subclass are identified. Cloning is done using 4×96 well microtiter plates, plating 0.5 cells per well. After two weeks wells are inspected with an inverted microscope. Supernatant is collected from wells positive for growth and production of anti-CD154 monoclonal antibodies is evaluated by ELISA. Positive hybridomas are subcloned and the produced antibody is isolated by affinity from 1–2L supernatant. Hybridoma # 207.2 is selected yielding the Antibody ABI793 and the produced Antibody is purified by affinity chromatography on a protein A column.

Antibody ABI793 is characterized by DNA and amino acid sequences as given in SEQ. ID. Nos. 1 to 4.

EXAMPLE 2

Determination of Dissociation Equilibrium Constant

The association and dissociation rate constant for the binding of recombinant human CD154 to ABI793 is determined by BIAcore analysis. ABI793 is immobilized, and binding of soluble recombinant CD154 (CD154-κ) in a concentration range from 10 to 160 nM is measured by surface plasmon resonance. The chosen format represents a monovalent interaction. Data analysis is performed using the BIA evaluation software.

| Association rate constant | $[M^{-1} xs^{-1}]$ (n = 3) | $(2.34 \pm 0.13) \times 10^4$ |
|---|---|---|
| Dissociation rate constant | $[s^{-1}]$ (n = 3) | $(5.38 \pm 0.43) \times 10^{-4}$ |
| Dissociation equilibrium constant $K_D$ | [nM] (n = 3) | $23.1 \pm 2.8$ |

EXAMPLE 3

Epitope Analysis

Figure 1:
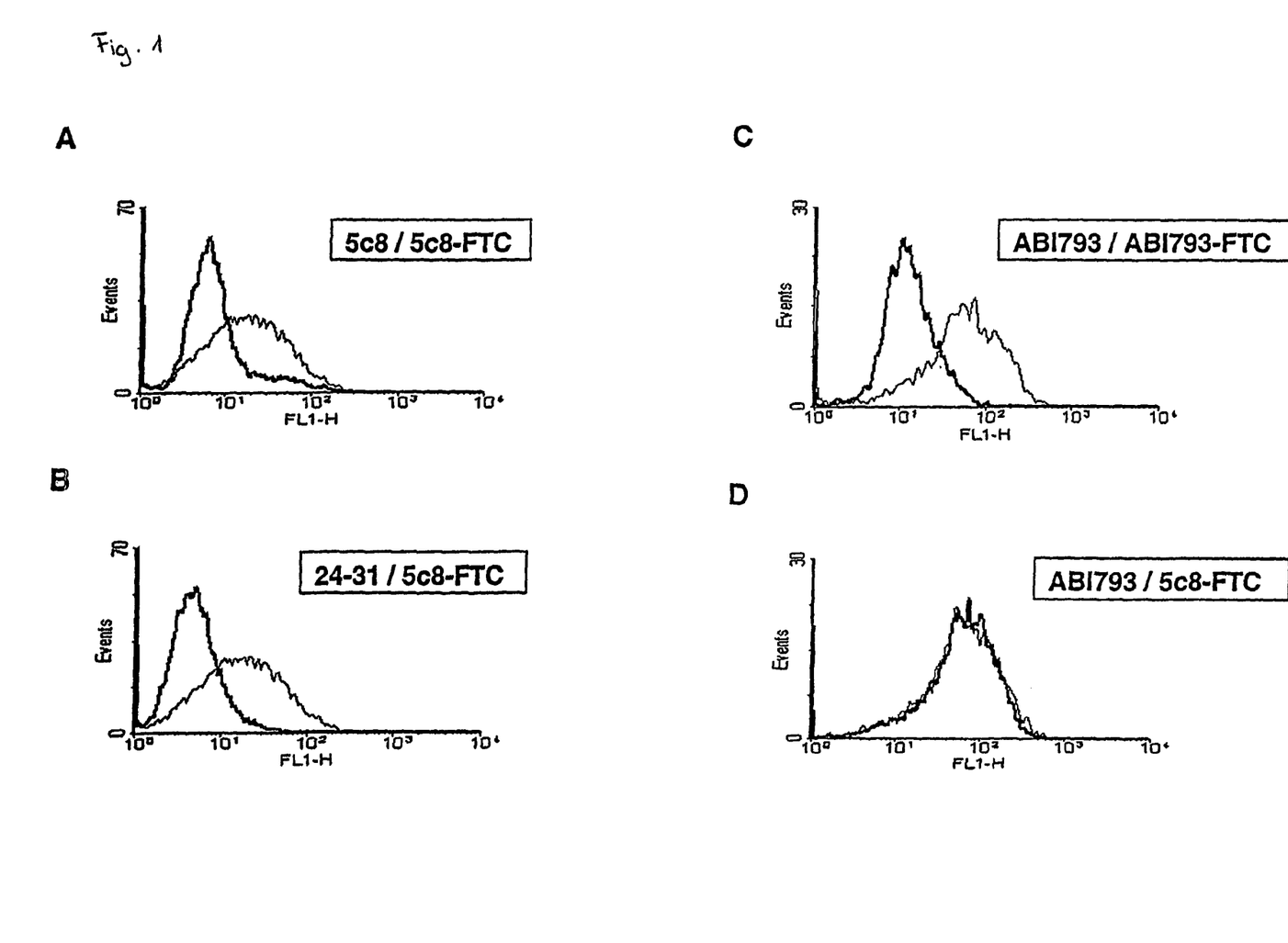
FIG. 1 refers to the epitope analysis and shows cross-blocking experiment results using Jurkat D1.1 cells: staining with FTC-labeled mAbs as indicated, alone (regular line) or after prior pre-incubation with the indicated unlabeled ant-CD154 mAb (bold line).
Figure 2:
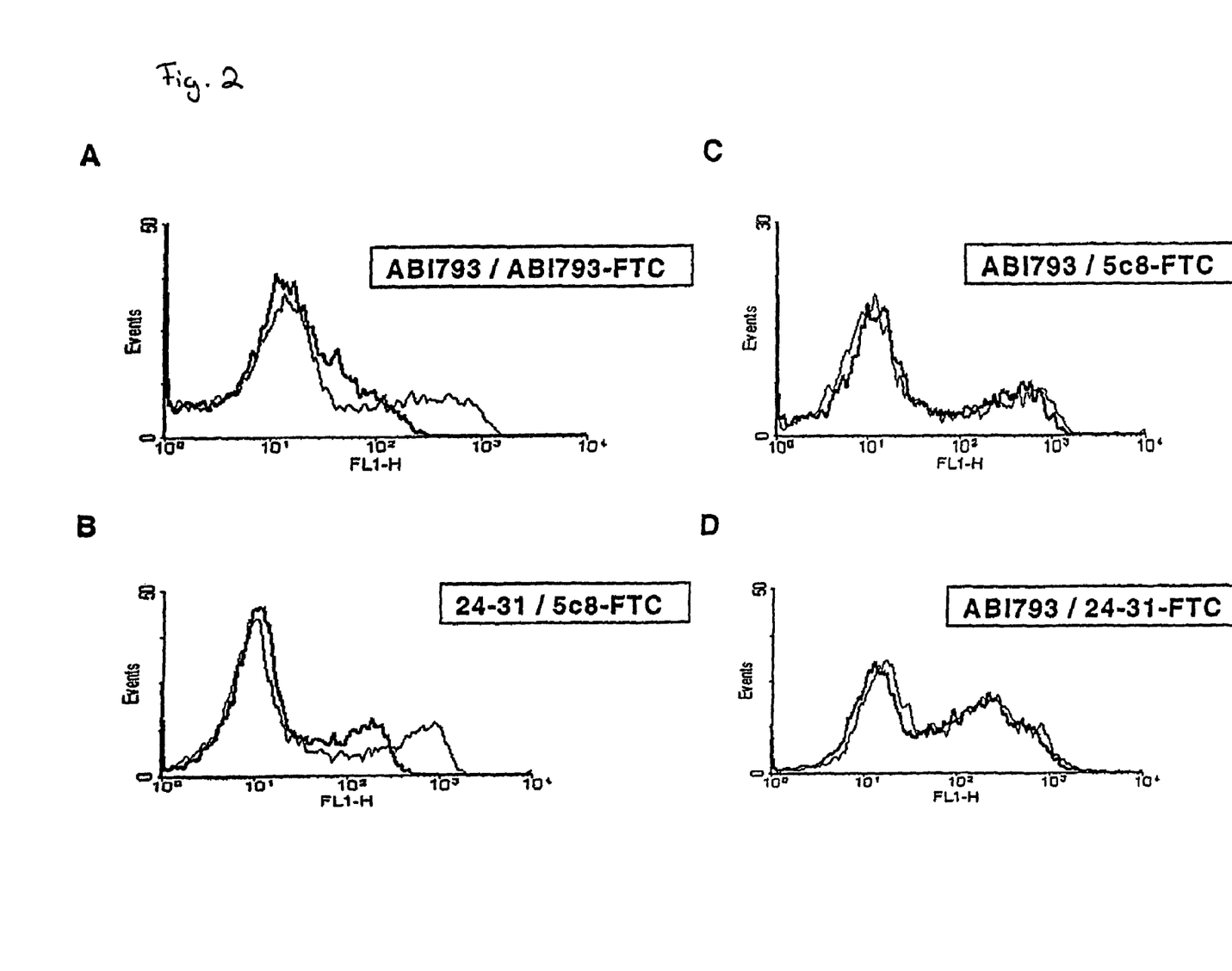
FIG. 2 refers to the epitope analysis and shows cross-blocking experiment results using activated human T cells: as in FIG. 1 but using purified CD4-positive human T cells which were activated for 6 hours with PMA/ionmycin prior to staining.
Figure 3:
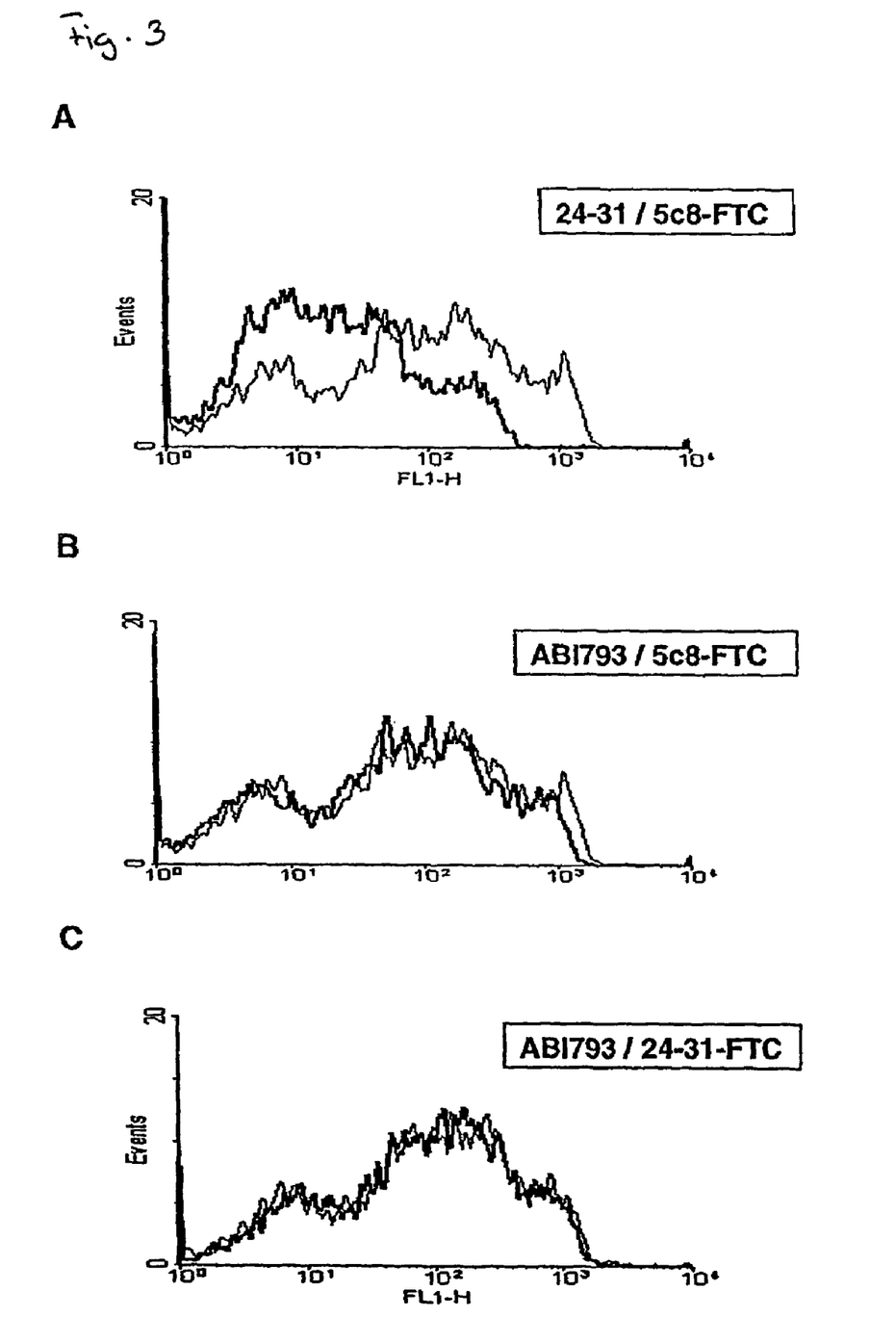
FIG. 3 refers to the epitope analysis and shows cross-blocking experiment results using activated cynomolgus monkey T cells: as in FIG. 1 but using purified CD4-positive cynomolgus monkey T cells which were activated for 4 hours with PMA/ionmycin prior to staining.

Cross-blocking experiments are performed in the presence of the mouse anti-CD154 MAbs 5c8 and 24-31: surface CD154-expressing T cells are stained with one of the three, for this purpose FTC-labelled, anti-CD154 Mabs. Preincubation of Jurkat D1.1 cells (which constitutively express CD154) with unlabelled 24-31 prior to staining with FTC-5c8 abolishes the fluorescent signal, i.e. blocks the binding of FTC-5c8 in the same way as does pre-incubation with unlabelled 5c8 (FIGS. 1A vs 1B). This indicates that 5c8 and 24-31 recognize a mutual or juxtaposed epitope(s) on the CD154 antigen. In contrast, pre-incubation with unlabelled ABI793 does not affect binding of FTC-labelled 5c8 (FIG. 1D). This demonstrates that ABI793 recognizes an epitope on the CD154 antigen which is different from the epitope(s) recognized by the mouse anti-human CD154 Mabs 5c8 and 24-31. These results are confirmed using PMA/ionomycin-activated, isolated CD154-positive T cells of either human (FIG. 2) or cynomolgus monkey (FIG. 3) origin. In these binding assays, using the same procedure as disclosed for the Jurkat cells, ABI793 recognizes an epitope on both the human as well as the cynomolgus monkey CD154 antigen which is different from the respective epitope(s) recognized by the mouse anti-human CD154 Mabs 5c8 and 24-31.

Figure 4:
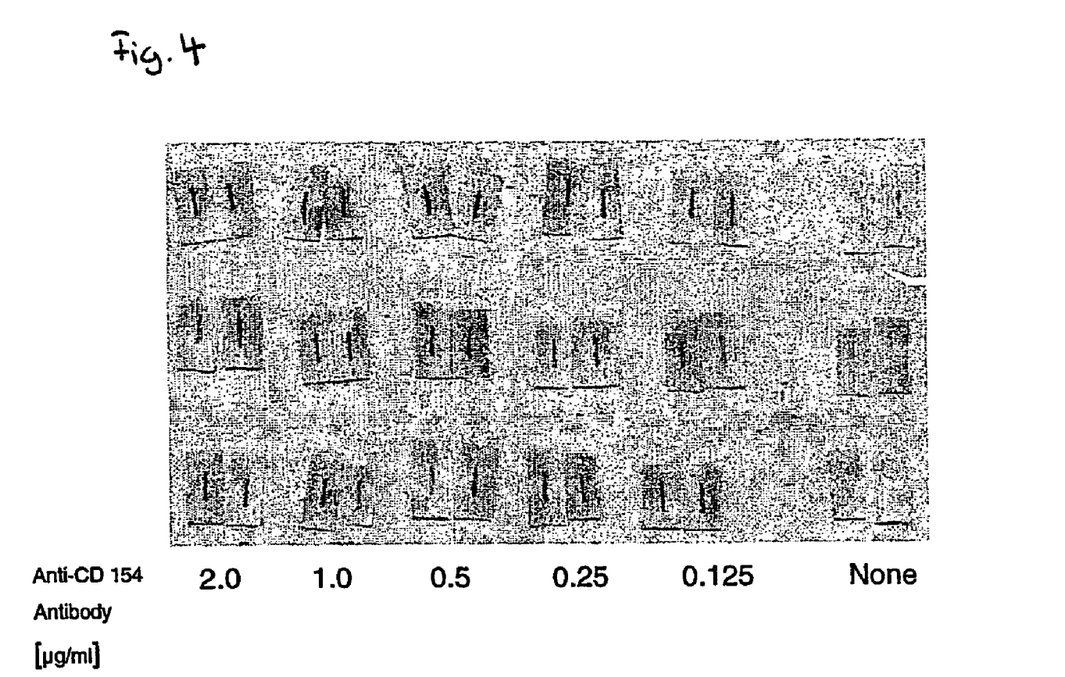
FIG. 4 shows the detection of the trimeric recombinant human CD154.

CD154 is expressed on T cells as a noncovalent homotrimer; likewise, the biologically active soluble CD154 forms spontaneously a noncovalent homotrimer in solution. To analyse whether the epitope recognized by ABI793 is dependent on the intact trimeric structure of CD154, slot blot (FIG. 4) and Western blot (FIG. 5) analyses is performed. FIG. 4 shows that trimeric CD154 (i.e., biologically active, soluble recombinant CD154) spotted onto a nitrocellulose membrane is recognized by ABI793 as well as by 5c8 and 24-31. This is in contrast to the results of the Western blot analyses. Under the conditions of polyacrylamide gel electrophoresis (PAGE) CD154 migrates as a monomer. After blotting to a nitrocellulose membrane only ABI793 is able to reveal the ca. 40 kD CD154 fusion protein (FIG. 5, "ABI793", lane 1, arrow "A") as well as the 15 kD bacterially expressed extracellular domain of CD154 (FIG. 5, "ABI793", lane 2, arrow "B"; the ca. 30 kD protein lighting up in this lane could potentially be a CD154 dimer). In contrast, 5c8 and 24-31 are unable to reveal either CD154 recombinant protein although these antibodies bind to recombinant CD154 spotted directly onto a nitrocellulose membrane (FIG. 4), i.e., to the trimeric form. This indicates that ABI793 recognizes both the CD154 monomer and trimer while 5c8 and 24-31 bind solely to the trimer. This corroborates the findings of the FACS studies which demonstrate that ABI793 recognizes an epitope on the CD154 antigen which is different from the one(s) recognized by 5c8 and 24-31.

Detection of the Trimeric Recombinant Human CD154:

1 µg of recombinant soluble human CD154 (i.e., the extracellular portion of human CD154 fused to mouse-$C_\kappa$) is slot-blotted onto a nitrocellulose filter. After blocking the membrane with 5% BSA, individual strips are incubated for 1 h with various concentrations of the anti-human CD154 antibodies (2.0; 1.0; 0.5; 0.25; 0.125 µg/ml). Bound antibody is then revealed by a 45-minute incubation with either alkaline phosphatase-coupled γ-chain-specific goat-anti-human IgG (for ABI793) or goat-anti-mouse IgG (for 5c8 and 24-31) followed by a standard reaction with BCIP/NBT. To control for cross-reaction with the mouse-$C_\kappa$ part of the recombinant CD154, strips are incubated with the respective second antibody only.

Figure 5:
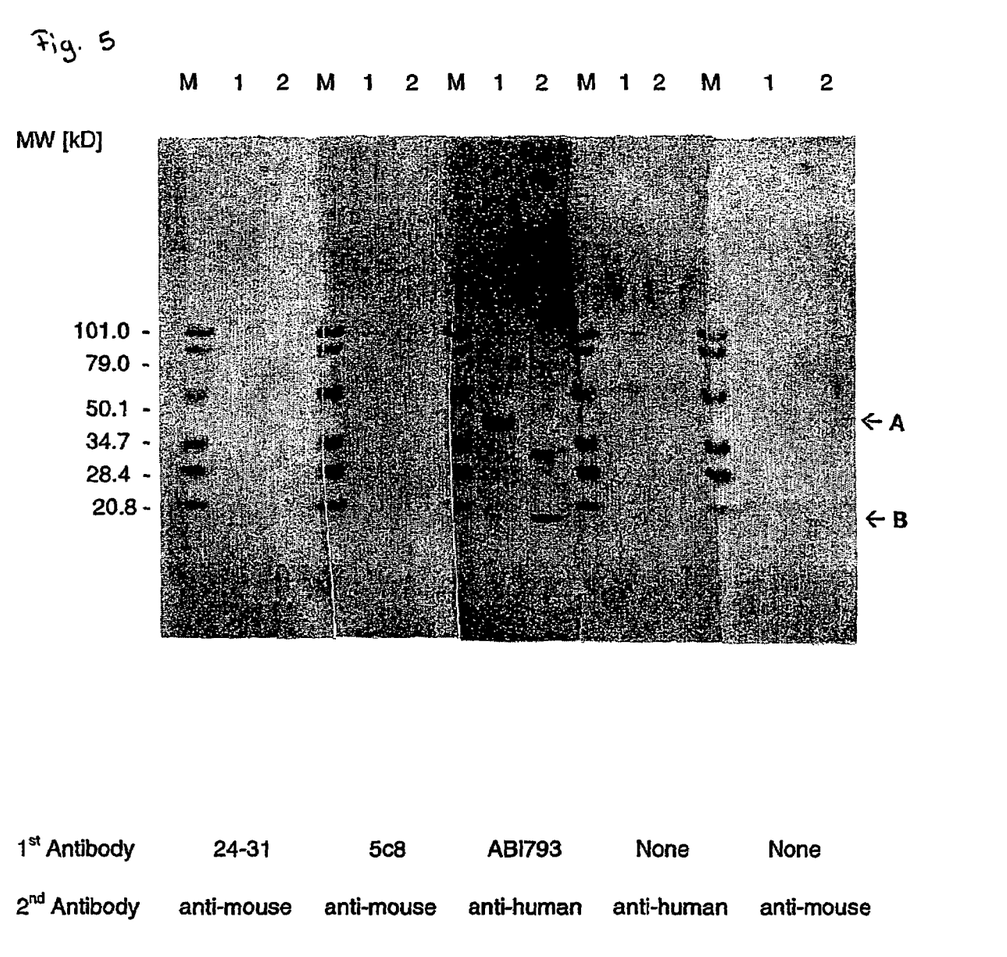
FIG. 5 shows the detection of monomeric recombinant human CD154 Lane M: pre-stained marker; Lane 1: human-CD154: mouse-$C_\kappa$ fusion protein; Lane 2: bacterially-expressed extracellular part of human CD154

Detection of Monomeric Recombinant Human CD154:

Five identical sample series of recombinant human CD154, either in form of a fusion protein consisting of the extracellular part of CD154 fused to mouse $C_\kappa$ or the extracellular portion only, expressed in E. coli, are electrophoresed on one 4–20% PAGE gradient gel. After blotting onto nitrocellulose the membrane is cut and the individual strips sequentially incubated for 1 hour each with the anti-human CD154 antibodies as indicated. Bound antibody is then revealed by a 45-minute incubation with an alkaline phosphatase-coupled γ-chain-specific second antibody (goat-anti-mouse IgG and goat-anti-human IgG, respectively), followed by a standard reaction with BCIP/NBT.

The invention claimed is:

1. An isolated CD154 binding molecule which comprises an antigen binding site comprising at least one immunoglobulin heavy chain variable domain ($V_H$) which comprises in sequence hypervariable regions CDR1, CDR2 and CDR3, said CDR1 having the amino acid sequence Asn-Phe-Ala-Phe-Asn (SEQ ID NO:5), said CDR2 having the amino acid sequence Arg-Ile-Leu-Pro-Ser-Leu-Asp-Ile-Ala-Ser (SEQ ID NO:6), and said CDR3 having the amino acid sequence Glu-Val-Asp-Gly-Gly-Gly-Phe (SEQ ID NO:7).

2. An isolated CD154 binding molecule comprising both heavy ($V_H$) and light chain ($V_L$) variable domains in which said CD154 binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence Asn-Phe-Ala-Phe-Asn (SEQ ID NO:5), said CDR2 having the amino acid sequence Arg-Ile-Leu-Pro-Ser-Leu-Asp-Ile-Ala-Ser (SEQ ID NO:6), and said CDR3 having the amino acid sequence Glu-Val-Asp-Gly-Gly-Gly-Phe (SEQ ID NO:7); and b) an immunoglobulin light chain variable domain ($V_L$) which comprises in sequence hypervariable regions CDR1', CDR2' and CDR3', said CDR1' having the amino acid sequence Arg-Ala-Ser-Gln-Gly-Ile-Ser-Ser-Trp-Leu-Ala (SEQ ID NO:8), said CDR2' having the amino acid sequence Ala-Ala-Ser-Ser-Leu-Gln-Ser (SEQ ID NO:9), and said CDR3' having the amino acid sequence Gln-Gln-Tyr-Asn-Ser-Tyr-Pro-Phe-Tyr (SEQ ID NO: 10).

3. An isolated CD154 binding molecule according to claim 2 which is a human antibody.

4. An isolated CD154 binding molecule which comprises at least bne binding site comprising a) one heavy chain which comprises a variable domain having the amino acid sequence of SEQ. ID. No. 2 and the constant part of a human heavy chain; and b) one light chain which comprises a variable domain having the amino acid sequence substantially of SEQ. ID. No. 4 and the constant part of a human light chain.

5. A recombinant DNA construct encoding a heavy chain or CD154 binding fragment thereof which comprises a) a first part which encodes a variable domain comprising alternatively framework and hypervariable regions, said hypervariable regions being in sequence CDR1, CDR2 and CDR3, the amino acid sequences of which are shown in SEQ. ID. No. 5, 6 and 7, respectively; the first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a stop codon.

6. A recombinant DNA construct encoding a light chain or CD154 binding fragment thereof which comprises a) a first part which encodes a variable domain comprising alternatively framework and hypervariable regions: said hypervariable regions being CDR1', CDR2' and CDR3', the amino acid sequences of which are shown in SEQ. ID. No. 8, 9 and 10, respectively; the first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the light chain and ends with a codon encoding the last amino acid of the constant part or fragment thereof followed by a stop codon.

7. An expression vector able to replicate in a prokaryotic or eukaryotic cell line which comprises at least one DNA constructs according to claim 5.

8. A pharmaceutical composition for use in the inhibition of an immun response mediated by CD154-positive cell interactions with CD40-positive cells, said composition comprising a CD154 binding molecule according to any of claims 2–4, 3in association with a pharmaceutically acceptable diluent or carrier therefor.

9. A pharmaceutical combination comprising a) a first agent which is a CD154 binding molecule according to any of claims 2–4, and b) at least one immunosuppressive, anti-inflammatory or chemotherapeutic agent.

10. A method of inhibiting an immune response mediated by CD154-positive cell interactions with CD40-positive cells, which method comprises administering to said subject an effective, non-toxic amount of a CD154 binding molecule according to any of claims 2–4.

11. A method according to claim 10 wherein said CD154 binding molecule is administered in combination with at least one immunosuppressive. anti-inflammatory or chemotherapeutic agent.

* * * * *